United States Patent
Carbanaru et al.

(10) Patent No.: US 8,165,694 B2
(45) Date of Patent: Apr. 24, 2012

(54) THERMAL MANAGEMENT OF IMPLANTABLE MEDICAL DEVICES

(75) Inventors: Rafeal Carbanaru, Valley Village, CA (US); Andrew DiGiore, Santa Monica, CA (US); Brett Schleicher, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 555 days.

(21) Appl. No.: 12/358,093

(22) Filed: Jan. 22, 2009

(65) Prior Publication Data

US 2009/0192575 A1 Jul. 30, 2009

Related U.S. Application Data

(60) Provisional application No. 61/024,458, filed on Jan. 29, 2008.

(51) Int. Cl.
*A61N 1/08* (2006.01)
(52) U.S. Cl. .......................................... 607/63
(58) Field of Classification Search ...................... 607/63
See application file for complete search history.

(56) References Cited

U.S. PATENT DOCUMENTS

| | | | |
|---|---|---|---|
| 4,041,955 A | 8/1977 | Kelly et al. | |
| 4,991,582 A | 2/1991 | Byers et al. | |
| 5,193,539 A | 3/1993 | Schulman et al. | |
| 5,193,540 A | 3/1993 | Schulman et al. | |
| 5,312,439 A | 5/1994 | Loeb | |
| 5,324,316 A | 6/1994 | Schulman et al. | |
| 5,405,367 A | 4/1995 | Schulman et al. | |
| 5,573,550 A | 11/1996 | Zadeh et al. | |
| 5,991,665 A | 11/1999 | Wang et al. | |
| 6,051,017 A | 4/2000 | Loeb et al. | |
| 6,293,899 B1 | 9/2001 | Sioshansi et al. | |
| 6,364,899 B1 | 4/2002 | Dobak, III | |
| 6,882,881 B1 | 4/2005 | Lesser et al. | |
| 6,894,456 B2 * | 5/2005 | Tsukamoto et al. | 320/107 |
| 6,971,391 B1 | 12/2005 | Wang et al. | |
| 7,048,756 B2 | 5/2006 | Eggers et al. | |
| 7,068,491 B1 | 6/2006 | Burdon et al. | |

(Continued)

FOREIGN PATENT DOCUMENTS

EP 1779869 A1 5/2007

(Continued)

OTHER PUBLICATIONS

Cameron, Tracy et al., Micromodular Implants to Provide Electrical Stimulation of Paralyzed Muscles and Limbs, IEEE Transaction of Biomedical Engineering, vol. 44, No. 9, pp. 781-790, Sep. 1997.

(Continued)

*Primary Examiner* — Brian T Gedeon
(74) *Attorney, Agent, or Firm* — Vista IP Law Group LLP (57) ABSTRACT

Systems and techniques for thermal management of implantable medical devices. In one aspect an implantable device includes an active component configured to perform medical activities, a charging component configured to convert energy from outside a body in which the implantable device is implanted into potential energy, and a thermal barrier between the charging component and the active portion. The thermal barrier thermally isolates the charging component from the active portion so that thermal resistance between the charging component and the active component is above the thermal resistance between the charging component and the body.

13 Claims, 7 Drawing Sheets

U.S. PATENT DOCUMENTS

| | | |
|---|---|---|
| 7,751,897 B2 * | 7/2010 | Single .................... 607/57 |
| 2003/0171792 A1 | 9/2003 | Zarinetchi et al. |
| 2004/0064163 A1 | 4/2004 | Aamodt et al. |
| 2004/0172090 A1 | 9/2004 | Janzig et al. |
| 2005/0096702 A1 | 5/2005 | Denker et al. |
| 2005/0149123 A1 | 7/2005 | Lesser et al. |
| 2006/0259093 A1 | 11/2006 | Stevenson et al. |
| 2007/0060970 A1 | 3/2007 | Burdon et al. |
| 2007/0096863 A1 | 5/2007 | Valencia Avila et al. |
| 2007/0260294 A1 * | 11/2007 | Schulman et al. ........... 607/60 |

FOREIGN PATENT DOCUMENTS

| | | |
|---|---|---|
| GB | 1482281 | 8/1977 |
| WO | WO 98/37926 A1 | 9/1998 |
| WO | WO 98/43700 A1 | 10/1998 |
| WO | WO 98/43701 A1 | 10/1998 |
| WO | WO 99/06108 A1 | 2/1999 |
| WO | WO 99/51301 A1 | 10/1999 |
| WO | WO 99/51302 A1 | 10/1999 |
| WO | WO 99/51303 A1 | 10/1999 |
| WO | WO 99/66985 A1 | 12/1999 |
| WO | WO 00/27477 A1 | 5/2000 |
| WO | WO 01/28622 A2 | 4/2001 |
| WO | WO 01/28628 A1 | 4/2001 |
| WO | WO 01/073883 A2 | 10/2001 |
| WO | WO 03/039660 A1 | 5/2003 |
| WO | WO 2007/035332 A1 | 3/2007 |
| WO | WO 2007/035443 A1 | 3/2007 |
| WO | WO 2007/117942 A2 | 10/2007 |

OTHER PUBLICATIONS

International Search Report dated Dec. 3, 2009 for PCT/US2009/032060, Form PCT/ISA/210 and 220 (7 pages).

Written Opinion of the International Searching Authority dated Dec. 3, 2009 for PCT/US2009/032060, Form PCT/ISA/237 (5 pages).

International Preliminary Report on Patentability dated Aug. 12, 2010 for PCT/US2009/032060, Form PCT/IB/373 (6 pages).

* cited by examiner

THERMAL MANAGEMENT OF IMPLANTABLE MEDICAL DEVICES

RELATED APPLICATION DATA

The present application claims the benefit under 35 U.S.C. §119 to U.S. Provisional Patent Application Ser. No. 61/024,458, filed Jan. 29, 2008. The foregoing application is hereby incorporated by reference into the present application in its entirety.

BACKGROUND

This disclosure relates to thermal management of implantable medical devices.

When the temperature of living cells and tissues is changed, the physiological structures, compositions, and processes of the cells and tissues can also change. For example, reaction kinetics, rates of mass transport, and the stability of cellular structures are all functions of temperature. Temperature changes are often harmful and cause departures from the preferred physiological states of cells and tissues. In extreme cases, thermal necrosis (i.e., cell death due to temperature) can result.

SUMMARY

Systems and techniques for thermal management of implantable medical devices are described. In one aspect, an implantable device includes an active component configured to perform medical activities, a charging component configured to convert energy from outside a body in which the implantable device is implanted into potential energy, and a thermal barrier between the charging component and the active portion. The thermal barrier thermally isolates the charging component from the active portion so that thermal resistance between the charging component and the active component is above the thermal resistance between the charging component and the body.

This and other aspects can include one or more of the following features. The thermal conductance between the charging component and the body can be 1.5, 2.0, 3.0, 5.0, or more times the thermal conductance between the charging component and the active component. The active component can include an implantable pulse generator configured to deliver electrical pulses to tissue, such as a microstimulator.

The charging component can include a coil configured to respond to an electric or magnetic field generated outside the body. The implantable device can include a lead that allows the active component to access the potential energy from the charging component. The thermal barrier can include a separation between the active component and the charging component spanned by the lead. The lead can be flexible and flex when subject to physiological-scale stresses associated with implantation.

The active component can include an implantable pulse generator configured to deliver electrical pulses to tissue. The charging component can include an electrode that is electrically connected to the implantable pulse generator for delivery of the electrical pulses. The charging component can include a flapped appendage that is mechanically joined to the active component at the thermal barrier. The thermal barrier can have a smaller area than an area of barriers that isolate the charging component from the body.

The charging component can include a first flapped appendage that is mechanically joined to the active component at a first thermal barrier and a second flapped appendage that is mechanically joined to the active component at a second thermal barrier. The active component can include circuitry to manage performance of the medical activities.

In another aspect, an implantable device includes an implantable pulse generator configured to deliver electrical pulses to tissue of a body over one or more electrodes. The implantable pulse generator can include a thermally insensitive portion that comprises a charging component configured to convert energy from outside a body in which the implantable pulse generator is implanted into potential energy, wherein the conversion is accompanied by a change in temperature, a thermally sensitive portion that comprises a component whose function or lifespan can be impaired by the change in temperature accompanying the conversion of energy from outside the body into potential energy by the charging component, and a thermal barrier between the thermally insensitive portion and the thermally sensitive portion. The thermal barrier can thermally isolate the thermally insensitive portion from the thermally sensitive portion so that thermal resistance between the thermally insensitive portion and the thermally sensitive portion is above the thermal resistance between the thermally insensitive portion and the body.

This and other aspects can include one or more of the following features. The thermal conductance between the thermally insensitive portion and the body is 1.5 or more times the thermal conductance between the thermally insensitive portion and the thermally sensitive portion. The implantable device can include a lead that allows the thermally sensitive portion to access the potential energy from the charging component. The thermal barrier can include a separation between the thermally sensitive portion and the thermally insensitive portion spanned by the lead.

The thermally insensitive portion can include the one or more electrodes. The thermally insensitive portion can include a flapped appendage that is mechanically joined to the thermally insensitive portion at the thermal barrier. The thermal barrier can have a smaller area than an area of barriers that isolate the thermally insensitive portion from the body. The thermally insensitive portion can include the one or more electrodes. The charging component can include a coil configured to respond to an electric or a magnetic field generated outside the body.

In another aspect, an implantable device includes a microstimulator dimensioned to be implanted in a body through a cannula of a surgical tool for performing closed surgical procedures. The microstimulator is configured to deliver electrical pulses to tissue of a body in which the microstimulator is implanted over one or more electrodes. The microstimulator includes a charging coil configured to convert an electric field or a magnetic field generated outside the body into potential energy, wherein the conversion is accompanied by a change in temperature, electrical circuitry to manage delivery of the electrical pulses to the tissue of the body, and a thermal barrier between the charging coil and the electrical circuitry, wherein the thermal barrier thermally isolates the charging coil from the electrical circuitry so that thermal resistance between the charging coil and the electrical circuitry is above the thermal resistance between the charging coil and the body.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like components.

DETAILED DESCRIPTION

Figures 1, 2, 3:
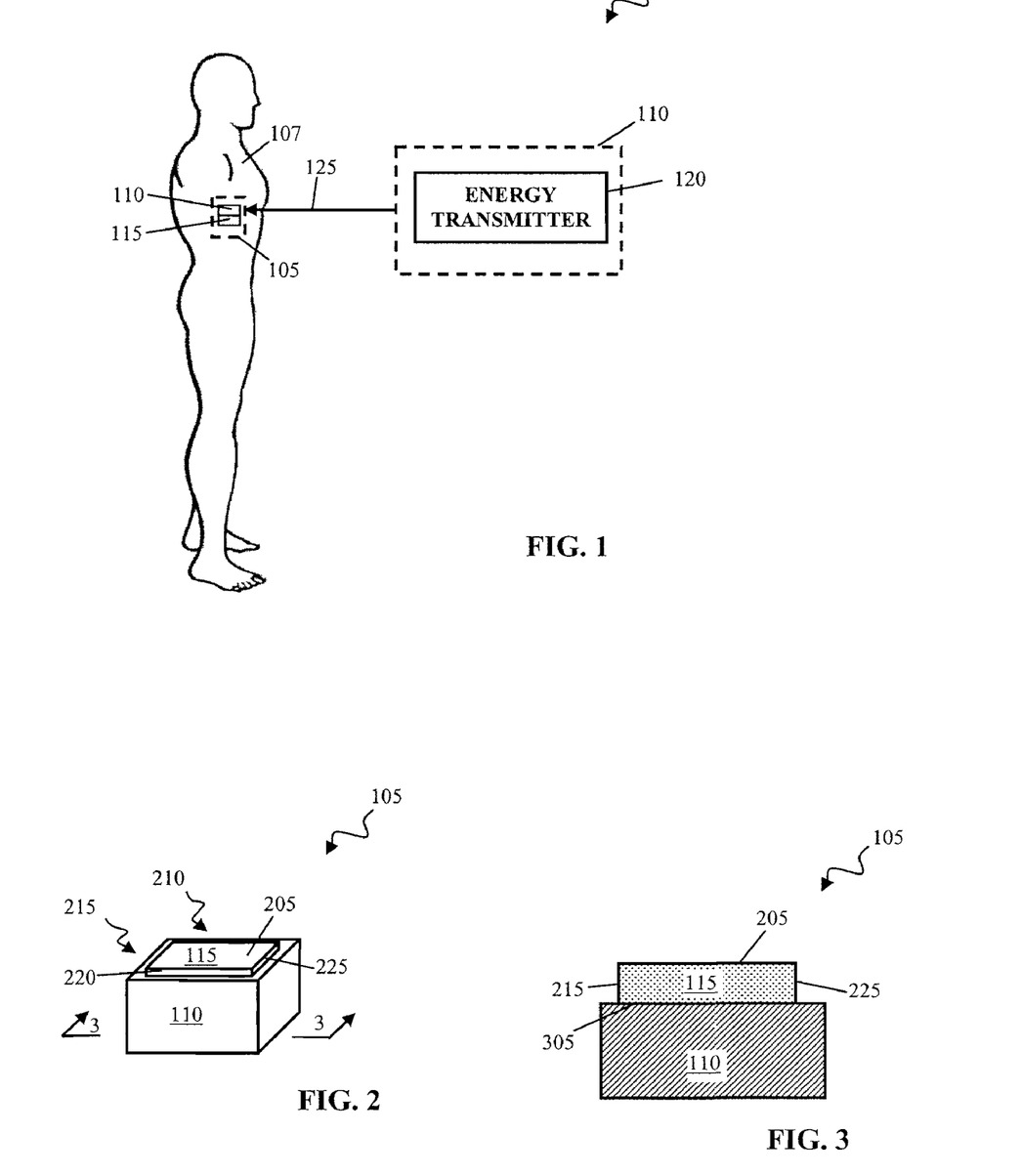
FIG. 1 shows a system in which the temperature of an implanted device is managed.
FIGS. 2-15 are schematic representations of implantable portions of the system of FIG. 1 in which excess heat generated in the conversion of energy into potential energy by charging components is managed.

FIG. 1 shows a system 100 in which the temperature of an implanted device is managed. System 100 can include an implantable portion 105 and an external (i.e., extracorporeal) portion 110. Implantable portion 105 is a device that is adapted for implantation in a body 107. For example, implantable portion 105 can include one or more hermetically-sealed, biocompatible housings adapted to reduce the immune response and/or cell necrosis associated with the implantation of portion 105 and to isolate the interior of implantable portion 105 from the body.

Implantable portion 105 includes an active component 110 and a charging component 115. Active component 110 is a device that performs diagnostic, therapeutic, restorative, prophylactic, monitoring, or other medical activities while implanted in the body. Active component 110 can include circuitry that manages the performance of these activities, as well as one or more power storage devices that stores energy consumed by the performance of these activities. For example, active component 110 can include electrical circuitry such as memory, timers, memory controllers, and machine logic such as logic gates, processors, ASIC's, and the like, along with power storage devices such as batteries, supercapacitors, fuel cells, mechanical energy storage devices, and the like.

The performance of activities by active component 110 consumes the energy stored at such power storage devices. Charging component 115 opposes this consumption of energy by converting energy from outside the body into potential energy. For example, in some implementations, charging component 115 is a conducting coil that can respond to a magnetic or electric field generated outside a body. In other implementations, charging component 115 is a photovoltaic component that can respond to light or other electromagnetic radiation generated outside the body. In other implementations, charging component 115 is a mechanical component such as a piezoelectric resonator that can respond to acoustic oscillations or other mechanical impulses generated outside the body. The potential energy from charging component 115 can be stored at an energy storage device in active component 110.

External portion 110 includes an energy transmitter 120 that generates an energy transmission 125. At least a portion of energy transmission 125 enters the body in which implantable portion 105 is implanted and interacts with charging component 115. Charging component 115 responds to the interaction with energy transmission 125 by converting energy transmission 125 into potential energy. For example, in some implementations, energy transmitter 120 is a biased coil that generates a magnetic or electric field transmission 125 that interacts with a conducting coil charging component 115. In other implementations, energy transmitter 120 is a laser, a bulb, or other light source that generates an electromagnetic radiation transmission 125 that interacts with a photovoltaic charging component 115. In other implementations, energy transmitter 120 is a piezoelectric crystal or other pressure source that generates a mechanical impulse transmission 125 that interacts with a mechanical charging component 115.

In real devices, the conversion of energy into potential energy by charging component 115 generates excess heat. For example, conducting coils have a finite resistance and heat when current flows. As another example, the conversion efficiency of photovoltaic and piezoelectric devices is not ideal. The present inventors have developed approaches for management of this excess heat.

FIGS. 2 and 3 are schematic representations of an implantable portion 105 in which excess heat generated in the conversion of energy into potential energy by charging component 115 is managed. Charging component 115 of implantable portion 105 is defined by a collection of barriers, which can be denoted for the sake of convenience as a top barrier 205, a rear barrier 210, a left side barrier 215, a front barrier 220, a right side barrier 225, and a bottom barrier 305. Barriers 205, 210, 215, 220, 225 isolate charging component 115 from a body when implantable portion 105 is implanted. Barriers 205, 210, 215, 220, 225 can be biocompatible in that they are adapted to reduce the immune response and/or cell necrosis associated with implantation.

Barrier 305 thermally isolates charging component 115 from active component 110, including any circuitry and power storage device(s) therein. The thermal isolation provided by barrier 305 can hinder heat transport from charging component 115 to active component 110. For example, barrier 305 can raise the thermal resistance between charging component 115 and active component 110 above the thermal resistance between charging component 115 and the body. In other words, the thermal conductance across barriers 205, 210, 215, 220, 225 can be higher than the thermal conductance across barrier 305. For example, the collective thermal conductance across barriers 205, 210, 215, 220, 225 can be 1.5 times, two times, three times, or five or more times higher than the thermal conductance across barrier 305.

The elevated thermal resistance of barrier 305 relative to barriers 205, 210, 215, 220, 225 can be achieved in a number of different ways. For example, one or more of barriers 205, 210, 215, 220, 225, 305 can passively or actively manage the flow of heat. For example, barrier 305 can be made from a material of lower thermal conductivity than a material from which one or more of barriers 205, 210, 215, 220, 225 are made. As another example, barrier 305 can be made thicker than one or more of barriers 205, 210, 215, 220, 225. As yet another example, the area of barrier 305 can be dimensioned to be smaller than the area of one or more of barriers 205, 210, 215, 220, 225. As a still further example, an active fluid flow device or a passive thermal conductor component can conduct heat one or more of barriers 205, 210, 215, 220, 225 and/or away from barrier 305. As another example, barrier 305 can include a phase transition material that captures excess heat by undergoing a phase transition. Combinations of these and other approaches can also be used.

Figure 4:
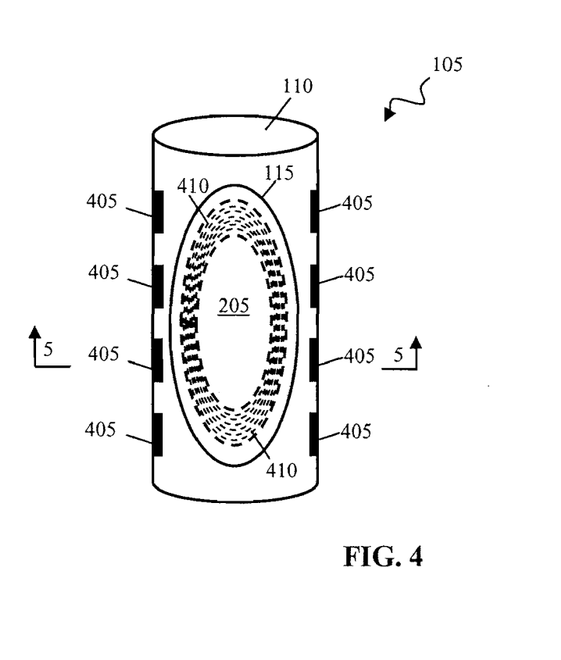
Figure 5:
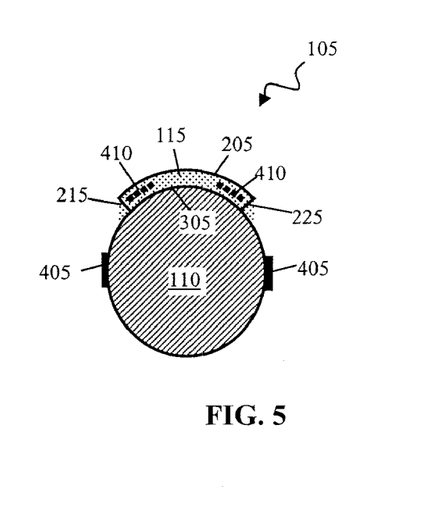

FIGS. 4 and 5 are schematic representations of an implantable portion 105 in which excess heat generated in the conversion of energy into potential energy by charging component 115 is managed. In the illustrated implementation, active component 110 includes an implantable pulse generator (IPG) that is configured to deliver electrical pulses to tissue. In such implementations, active component 110 can include one or more electrodes 405, such as one or more cathodes to electrically excite the depolarization of a nerve and/or muscle tissue and/or one or more anodes to hyperpolarize nerve and/or muscle tissue.

In some implementations, implantable portion 105 can be a microstimulator that is dimensioned to be implanted in a body through the cannula of a surgical tool for performing closed surgical procedures, such as an endoscopic or a laparoscopic device. One example of such a microstimulator is the multi-electrode BION microstimulator developed by Advanced Bionics (Sylmar, Calif.). The multi-electrode BION can be a leadless microstimulator that is formed from an ovoid cylinder that is about 30 millimeters in length and has a width of about 7.5 millimeters and a thickness of about 4.3 mm.

This form factor allows the BION to be implanted with relative ease and rapidity, e.g., via endoscopic or laparoscopic techniques. In some implementations, the BION consists of eight silicon electrodes that are disposed in groups of four on opposite sides of a biocompatible casing, as shown. Various features and details associated with the manufacture, operation, and use of BION implantable microstimulators are described in U.S. Pat. No. 5,193,539, U.S. Pat. No. 5,193,540, U.S. Pat. No. 5,312,439, U.S. Pat. No. 5,324,316, U.S. Pat. No. 5,405,367, U.S. Pat. No. 6,051,017, PCT Publication No. WO 98/37926, PCT Publication No. WO 98/43700, PCT Publication No. WO 98/43701, and the publication entitled "Micromodular Implants to Provide September Electrical Stimulation of Paralyzed Muscles and Limbs" by Cameron, et al. in IEEE Transactions on Biomedical Engineering, Vol. 44, No. 9, pages 781 790 (1997), the contents of all of which are incorporated herein by reference.

In the illustrated implementation, charging component 115 includes an internal conducting coil 410 that can respond to a magnetic or electric field generated outside a body. In particular, an external magnetic or electric field can drive electrons in coil 410. The motion of these electrons can be converted to potential energy and stored in a battery or other storage device.

Coil 410 is surrounded by barriers 205, 215, 225 that isolate coil 410 from a body when implantable portion 105 is implanted. Barrier 305 thermally isolates coil 410 from IPG component 110 to hinder heat transport from coil 410 to IPG component 110. In particular, the thermal conductance across barriers 205, 215, 225 is higher than the thermal conductance across barrier 305. For example, barrier 305 can be relatively thicker than barriers 205, 215, 225. As another example, barrier 305 can be made from a material with a relatively lower thermal conductivity. As yet another example, barrier 305 can include one or more phase transition materials that undergoes a phase transition in response to heating.

In some implementations, barriers 205, 215, 225 can be formed of a biocompatible material, such as a magnetically transparent biocompatible polymer. Examples of such biocompatible polymers include silicone, urethane, and the like. Barrier 305 can also such a biocompatible polymer, as well as one or more of the same materials that form the remainder of a biocompatible housing that houses IPG component 110. For example, barrier 305 can include a magnetically transparent ceramic such as zirconia. In some implementations, a ceramic and polymer can be laminated, glued, adhered, compression fitted, or otherwise joined together in a layered structure to form barrier 305. In some implementations, the polymer can be detached from the ceramic. For example, the polymer may be peeled away from the ceramic, an intermediate adhesive may be dissolved, and/or a compression fitting may be released.

In some implementations, charging component 115 can be a relatively thin, sheet-like member defined by an opposing pair of faces each having a relatively large area. Charging component 115 can be dimensioned to contact and follow the contour of active IPG component 110 with one of the relatively large area faces. Coil 410 can be positioned within charging component 115 so that the windings of coil 410 follow a path around normals to the larger faces of such a charging component 115. In some implementations, charging component 115 can be a flexible disk or ovoid structure and the windings of coil 410 can follow a path around the primary axis of the disk or ovoid structure.

Figure 6:
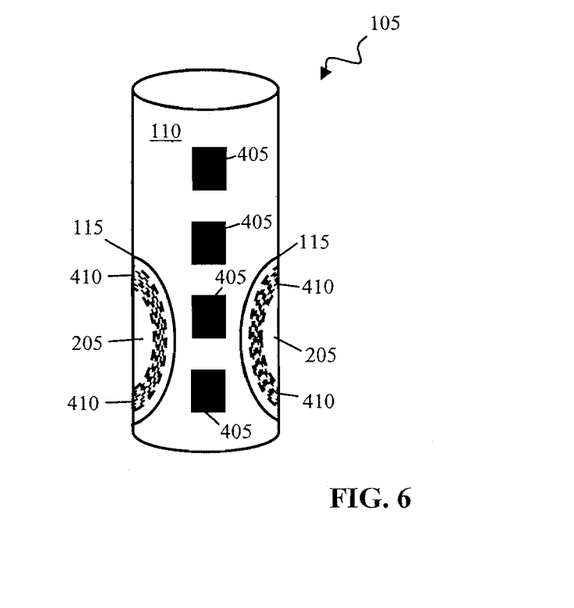

FIG. 6 is a schematic representation of another implantable portion 105 in which excess heat generated in the conversion of energy into potential energy by charging component 115 is managed. In the illustrated implementation, implantable portion 105 includes a microstimulator active component 110. Charging component 115 includes a pair of conducting coils 410 that are disposed on opposite sides of active component 110 in a charging component 115 that is dimensioned to contact and follow the contour of microstimulator active component 110. Both conducting coils 410 can respond to a magnetic or electric field generated outside a body.

Both conducting coils 410 are thermally isolated from active component 110 by barriers 305 in that the thermal conductance across barriers 205, 215, 225 is higher than the thermal conductance across barrier 305. For example, barriers 305 can be relatively thicker than barriers 205, 215, 225. As another example, barriers 305 can be made from a material with a relatively lower thermal conductivity. As yet another example, barriers 305 can include one or more phase transition materials that undergoes a phase transition in response to heating.

In some implementations, barriers 305 can be formed of the same materials as the remainder of a biocompatible housing that houses IPG component 110. For example, barriers 305 can be formed from a magnetically transparent ceramic such as zirconia. Further, barriers 205, 215, 225 can also be formed of a biocompatible material. For example, barriers 205, 215, 225 can be formed from a magnetically transparent biocompatible polymer.

Figure 7:
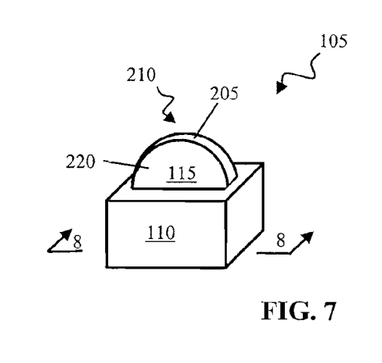
Figure 8:
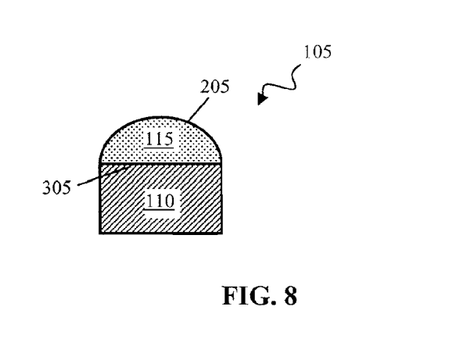

FIGS. 7 and 8 are schematic representations of an implantable portion 105 in which excess heat generated in the conversion of energy into potential energy by charging component 115 is managed. In the illustrated implementation, charging component 115 is defined by an arcular top barrier 205, rear barrier 210, and front barrier 220 as a flapped appendage that is mechanically joined to active component 110 at barrier 305. Charging component 115 is flapped in that it is relatively thin in comparison to its length and breadth and the flap of charging component 115 is positioned to extend outwardly away from active component 110 so that the area of barrier 305 is relatively small in comparison to the areas of rear barrier 210 and front barrier 220. This disposition of charging component 115 can make the thermal conductance across barrier 305 lower than the thermal conductance across barriers 210, 220, even when barriers 210, 220, 305 have otherwise comparable thermal conductivities and thicknesses.

In some implementations, flapped charging component 115 can be flexible in that relative motion and/or rotation between active component 110 and charging component 115 is achieved when implantable portion 105 is subject to physiological-scale stresses associated with implantation. In other implementations, flapped charging component 115 can be stiff in that active component 110 and charging component 115 are held in a fixed positional relationship when implantable portion 105 is subject to physiological-scale stresses associated with implantation. In either case, the outer surfaces of flapped charging component 115 can be biocompatible and adapted to reduce the immune response and/or cell necrosis associated with implantation.

Figure 9:
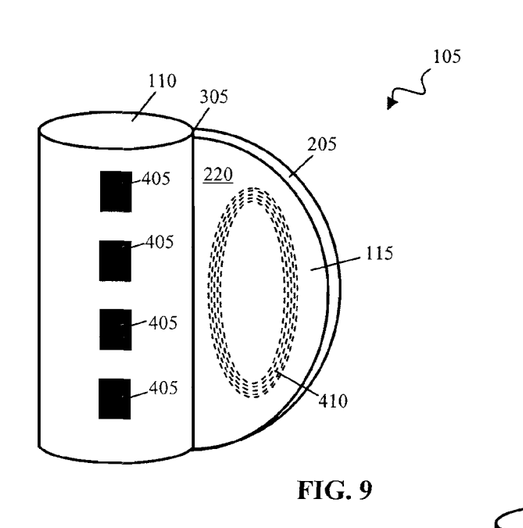

FIG. 9 is a schematic representation of another implantable portion 105 in which excess heat generated in the conversion of energy into potential energy by charging component 115 is managed. In the illustrated implementation, implantable portion 105 includes a microstimulator active component 110. Flapped charging component 115 includes a conducting coil 410 that can respond to a magnetic or electric field generated outside a body. Coil 410 can be positioned within flapped charging component 115 so that the windings of coil 410 follow a path around normals to the larger faces of flapped charging component 115.

The flap of charging component 115 is generally positioned to extend outwardly away from active component 110 so that the area of barrier 305 is relatively small in comparison to the areas of rear barrier 210 and front barrier 220. This disposition of charging component 115 can make the thermal conductance across barrier 305 lower than the thermal conductance across barriers 210, 220 even when barriers 210, 220, 305 have otherwise comparable thermal conductivities and thicknesses.

Figure 10:
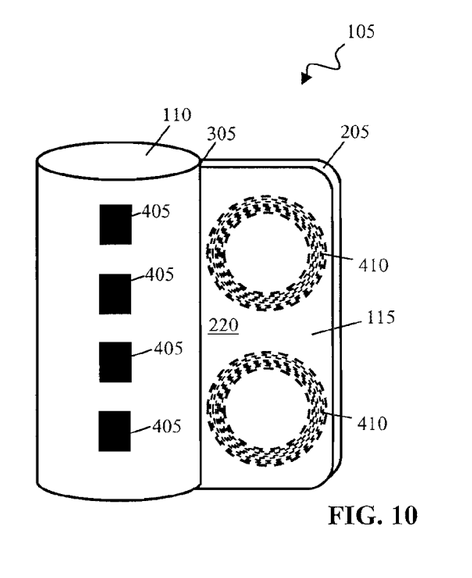

FIG. 10 is a schematic representation of another implantable portion 105 in which excess heat generated in the conversion of energy into potential energy by charging component 115 is managed. In the illustrated implementation, implantable portion 105 includes a microstimulator active component 110. A single flapped charging component 115 includes a pair of conducting coils 410 that can respond to a magnetic or electric field generated outside a body. Coils 410 can be positioned within flapped charging component 115 so that their windings follow a path around normals to the larger faces of flapped charging component 115.

The flap of charging component 115 is positioned to extend outwardly away from active component 110 so that the area of barrier 305 is relatively small in comparison to the areas of rear barrier 210 and front barrier 220. This disposition of charging component 115 can make the thermal conductance across barrier 305 lower than the thermal conductance across barriers 210, 220 even when barriers 210, 220, 305 have otherwise comparable thermal conductivities and thicknesses.

Figure 11:
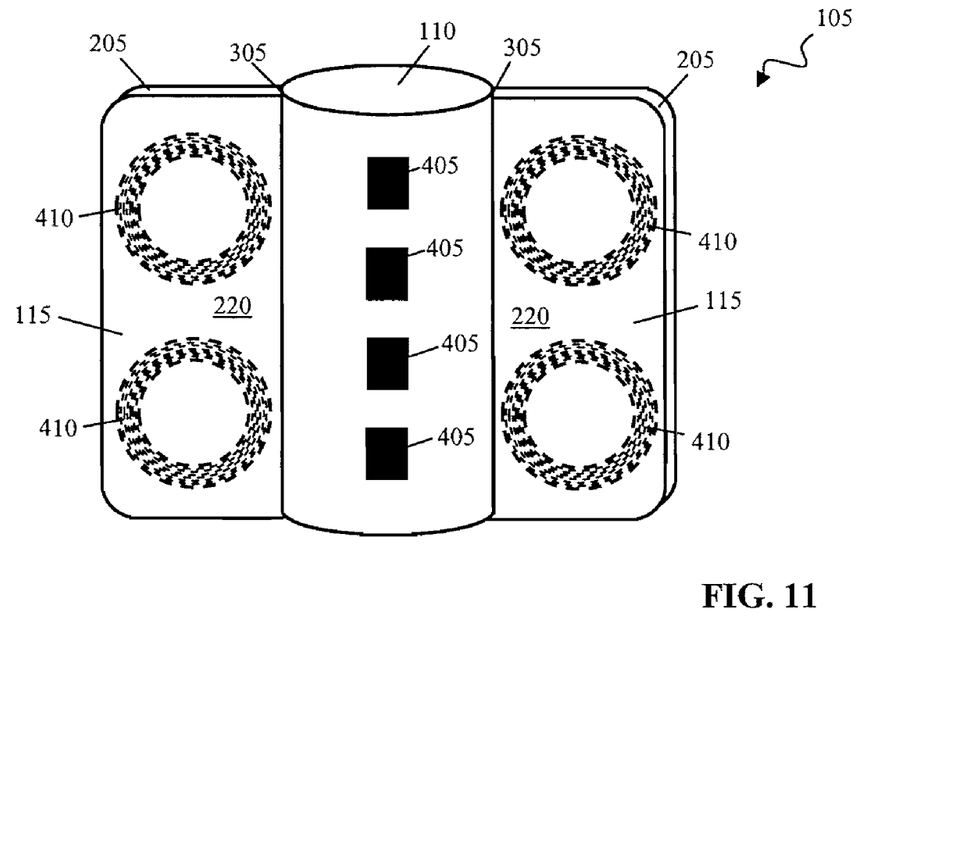

FIG. 11 is a schematic representation of another implantable portion 105 in which excess heat generated in the conversion of energy into potential energy by charging component 115 is managed. In the illustrated implementation, implantable portion 105 includes a microstimulator active component 110 and a pair of flapped charging component 115, each of which includes a pair of conducting coils 410 that can respond to a magnetic or electric field generated outside a body. Each of the coils 410 can be positioned within respective flapped charging components 115 so that their windings follow paths around normals to the larger faces of flapped charging components 115.

The flaps of charging components 115 are positioned to extend outwardly away from active component 110 so that the areas of barriers 305 are relatively small in comparison to the areas of rear barriers 210 and front barriers 220. This disposition of charging components 115 can make the thermal conductance across barriers 305 lower than the thermal conductance across barriers 210, 220 even when barriers 210, 220, 305 have otherwise comparable thermal conductivities and thicknesses.

Figure 12:
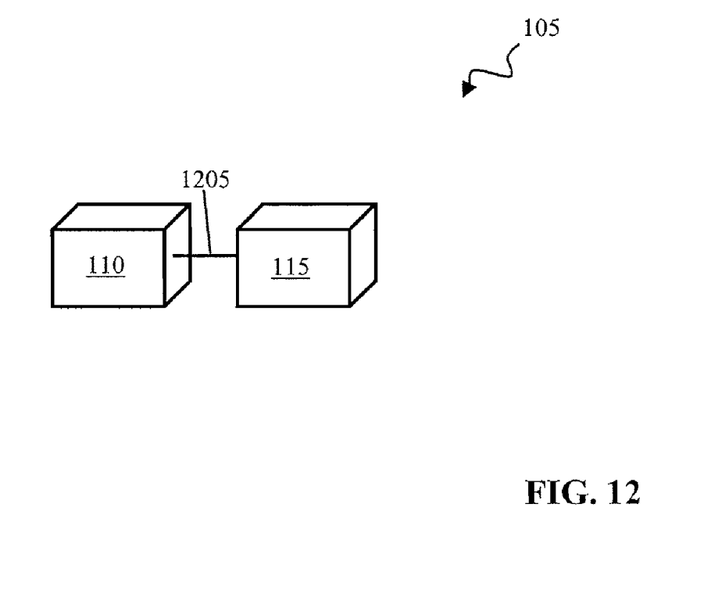

FIG. 12 is a schematic representation of an implantable portion 105 in which excess heat generated in the conversion of energy into potential energy by charging component 115 is managed. In the illustrated implementation, active component 110 and charging component 115 are joined only by a lead 1205. The separation between active component 110 and charging component 115 spanned by lead 1205 acts as a thermal barrier and thermally isolates charging component 115 from active component 110, including any circuitry and power storage device(s) therein. This thermal isolation can hinder heat transport from charging component 115 to active component 110 For example, the separation between active component 110 and charging component 115 can raise the thermal resistance between charging component 115 and active component 110 above the thermal resistance between charging component 115 and the body. This can be accomplished, e.g., with lead 1205 being longer than barriers that define charging component 115, with lead 1205 having a smaller area that than barriers that define charging component 115, and/or with lead 1205 having a smaller thermal conductivity than barriers that define charging component 115.

Lead 1205 includes wires or other components that allow the active component 110 to access the potential energy from charging component 115. In some implementations, lead 1205 can be flexible in that relative motion and/or rotation between active component 110 and charging component 115 is achieved when implantable portion 105 is subject to physiological-scale stresses associated with implantation. In other implementations, lead 1205 can be stiff in that active component 110 and charging component 115 are held in a fixed positional relationship when implantable portion 105 is subject to physiological-scale stresses associated with implantation. In either case, the outer surface of lead 1205 can be biocompatible and adapted to reduce the immune response and/or cell necrosis associated with implantation.

Figure 13:
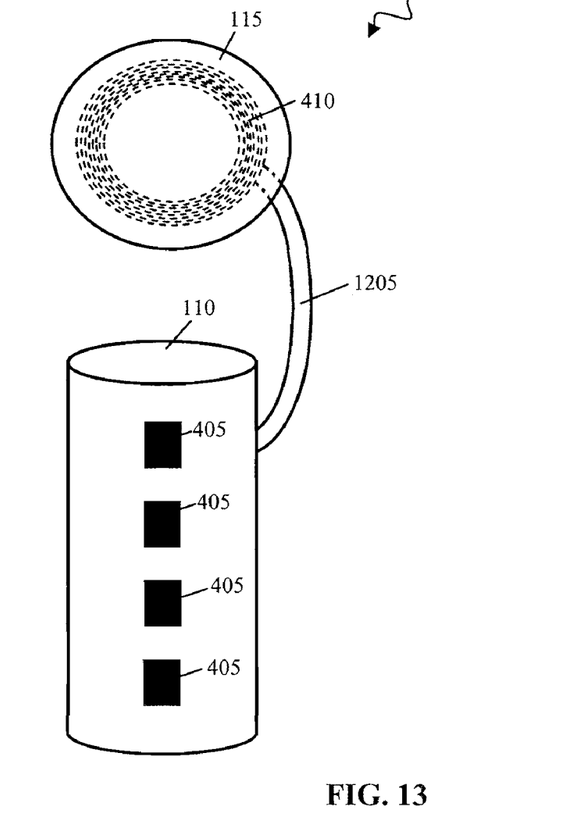

FIG. 13 is a schematic representation of an implantable portion 105 in which active component 110 and charging component 115 are joined only by lead 1205. In the illustrated implementation, implantable portion 105 includes a microstimulator active component 110. Charging component 115 includes a conducting coil 410 that can respond to a magnetic or electric field generated outside a body. With active component 110 and charging component 115 joined only by lead 1205, heat transport from charging component 115 to active component 110 is hindered.

Figure 14:
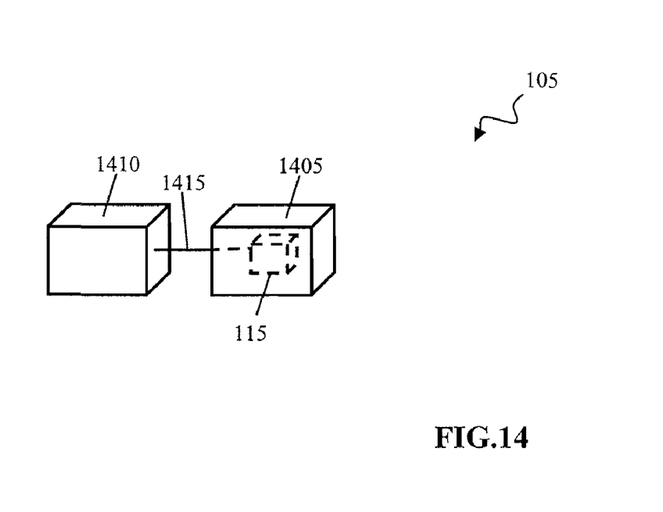

FIG. 14 is a schematic representation of an implantable portion 105 in which excess heat generated in the conversion of energy into potential energy by charging component 115 is managed. Implantable portion 105 includes a thermally insensitive portion 1405 and a thermally sensitive portion 1410 that are joined only by a lead 1415. Thermally insensitive portion 1405 includes charging component 115 and other components whose function and/or lifespan is not significantly impaired by changes in temperature of the magnitude that occur as a result of the conversion of energy from outside the body into potential energy by charging component 115. Thermally sensitive portion 1410 includes a collection of circuitry and/or other components whose function and/or lifespan can be impaired by changes in temperature of the magnitude that occur as a result of the conversion of energy from outside the body into potential energy by charging component 115.

The separation between thermally insensitive portion 1405 and thermally sensitive portion 1410 spanned by lead 1415 acts as a barrier that thermally isolates thermally insensitive portion 1405 from thermally sensitive portion 1410. This thermal isolation can hinder heat transport from thermally insensitive portion 1405 to thermally sensitive portion 1410. The separation between thermally insensitive portion 1405 and thermally sensitive portion 1410 can raise the thermal resistance between thermally insensitive portion 1405 and thermally sensitive portion 1410 above the thermal resistance between thermally insensitive portion 1405 and the body. This can be accomplished, e.g., with lead 1415 being longer than barriers that define thermally insensitive portion 1405, with lead 1415 having a smaller area that than barriers that define thermally insensitive portion 1405, and/or with lead 1415 having a smaller thermal conductivity than barriers that define thermally insensitive portion 1405.

Lead 1415 includes wires or other components that allow thermally sensitive portion 1410 to access the potential energy from thermally insensitive portion 1405, as well as other wires or components that allow thermally sensitive portion 1410 to interact with other components in thermally insensitive portion 1405. Lead 1415 can be flexible or lead 1415 can be stiff. The outer surface of lead 1415 can be biocompatible.

Figure 15:
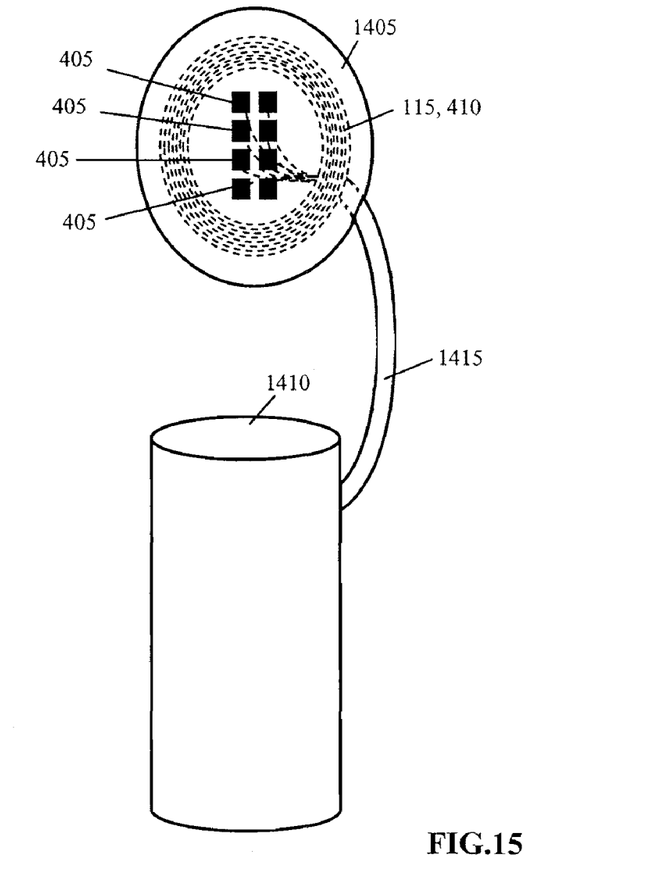

FIG. 15 is a schematic representation of an implantable portion 105 in which thermally insensitive portion 1405 and thermally sensitive portion 1410 are joined only by lead 1415. In the illustrated implementation, thermally sensitive portion 1410 includes many of the active components of a microstimulator, such as electrical circuitry such as memory, timers, memory controllers, and machine logic circuitry such as logic gates, processors, ASIC's, and the like, along with power storage devices such as batteries, supercapacitors, fuel cells, mechanical energy storage devices, and the like. In addition to charging component 115 that includes a conducting coil 410 that can respond to a magnetic or electric field generated outside a body, thermally insensitive portion 1405 includes a double row of electrodes 405 for delivering electrical pulses to tissue. With thermally insensitive portion 1405 and thermally sensitive portion 1410 joined only by lead 1415, heat transport from thermally insensitive portion 1405 to thermally sensitive portion 1410 is hindered.

Figure 16:
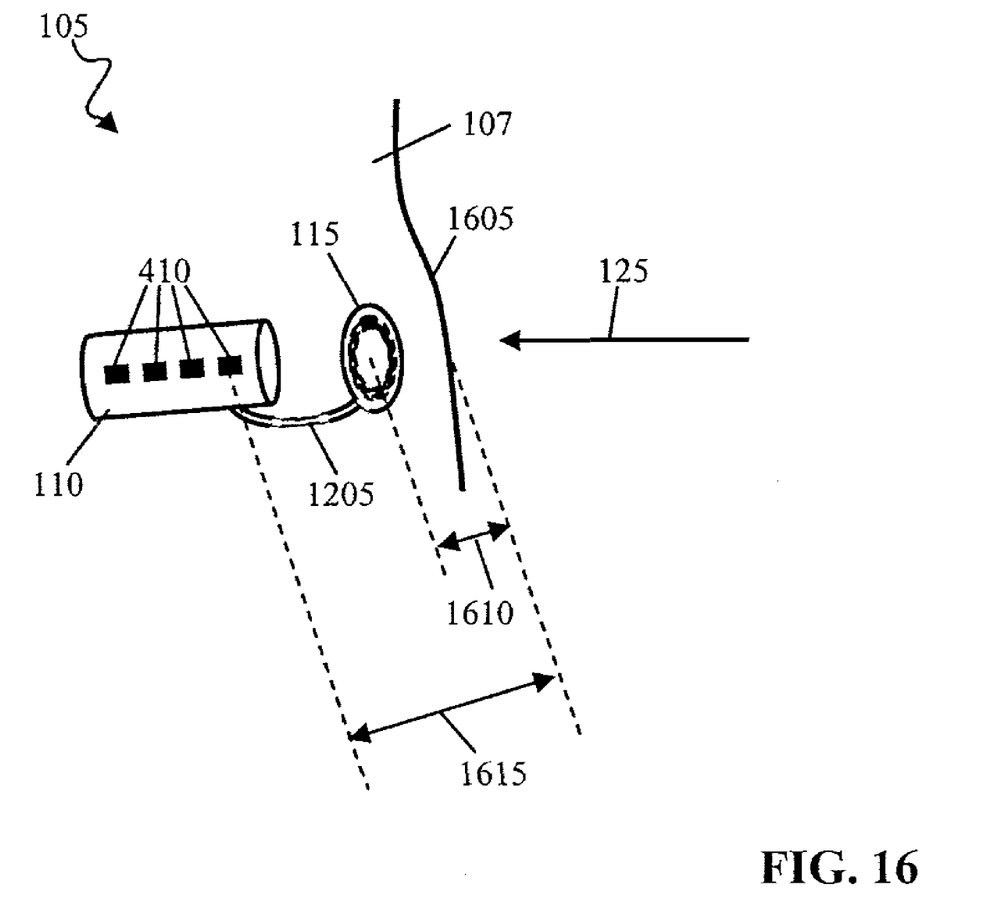
FIG. 16 schematically represents an implantation of an implantable portion of the system of FIG. 1 in a body.

FIG. 16 schematically represents an implantation of implantable portion 105 in body 107. Body 107 is defined by a skin surface 1605. Implantable portion 105 is implanted beneath skin surface 1605. Implantable portion 105 is oriented so that charging component 115 is a first distance 1610 beneath skin surface 1605 whereas electrodes 410 are a second, larger distance 1615 beneath skin surface 1605. Electrodes 410 can deliver electrical pulses to tissue with potential energy received from charging component 115 by active components 110.

With charging component 115 relatively close to skin surface 1605, a relatively large portion of energy transmission 125 may be captured by charging component 115 and converted into potential energy. At the same time, electrodes 410 can be positioned further beneath skin surface 1605 to deliver electrical pulses to cells and tissue further from skin surface 1605.

Figure 17:
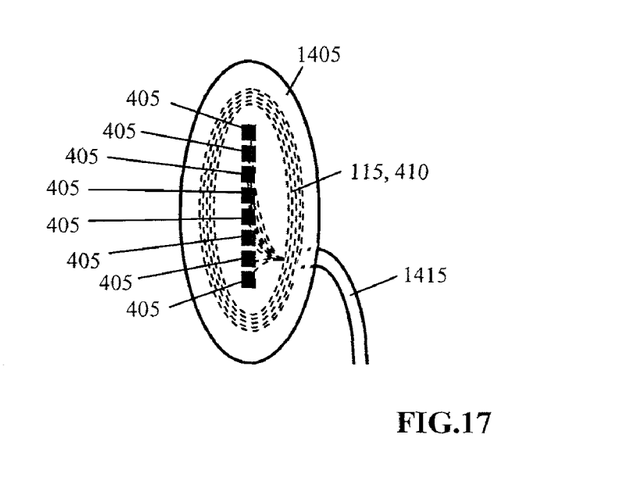
FIG. 17 schematically represents a thermally insensitive portion of an implantable portion of the system of FIG. 1.

A number of implementations have been described. Nevertheless, it will be understood that various modifications may be made. For example, photovoltaic charging components can convert sunlight into potential energy. As another example, as illustrated in FIG. 17, a thermally insensitive portion 1405 can include a single row of electrodes 405 for delivering electrical pulses to tissue. Accordingly, other implementations are within the scope of the following claims.

What is claimed is:

1. An implantable device comprising:
an active component configured to perform medical activities;
a charging component disposed on a surface of the active component, the charging component configured to convert energy from outside a body in which the implantable device is implanted into potential energy, the charging component having a planar surface that conforms to the surface of the active component; and
a thermal barrier disposed between the charging component and the active component, wherein the thermal barrier thermally isolates the charging component from the active component so that thermal resistance between the charging component and the active component is above the thermal resistance between the charging component and the body.

2. The implantable device of claim 1, wherein the thermal conductance between the charging component and the body is 1.5 or more times the thermal conductance between the charging component and the active component.

3. The implantable device of claim 1, wherein the active component comprises an implantable pulse generator configured to deliver electrical pulses to tissue.

4. The implantable device of claim 3, wherein the implantable pulse generator comprises a microstimulator.

5. The implantable device of claim 1, wherein the charging component is a coil configured to respond to an electric or magnetic field generated outside the body, wherein the thermal barrier is between the coil and the active component to thermally isolate the coil from the active component so that thermal resistance between the coil and the active component is above the thermal resistance between the coil and the body.

6. The implantable device of claim 1, wherein the active component comprises circuitry to manage performance of the medical activities.

7. An implantable pulse generator configured to deliver electrical pulses to tissue of a body over one or more electrodes, the implantable pulse generator comprising:
a thermally sensitive portion that comprises a component whose function or lifespan can be impaired by the change in temperature accompanying the conversion of energy from outside the body into potential energy by the charging component;
a thermally insensitive portion comprising a charging component configured to convert energy from outside a body in which the implantable pulse generator is implanted into potential energy, wherein the conversion is accompanied by a change in temperature, the thermally insensitive portion disposed on a surface of the thermally sensitive portion and having a planar surface that conforms to the surface of the thermally sensitive portion; and
a thermal barrier between the thermally insensitive portion and the thermally sensitive portion, wherein the thermal barrier thermally isolates the thermally insensitive portion from the thermally sensitive portion so that thermal resistance between the thermally insensitive portion and the thermally sensitive portion is above the thermal resistance between the thermally insensitive portion and the body.

8. The implantable device of claim 7, wherein the thermal conductance between the thermally insensitive portion and the body is 1.5 or more times the thermal conductance between the thermally insensitive portion and the thermally sensitive portion.

9. The implantable device of claim 7, wherein the thermally insensitive portion comprises the one or more electrodes.

10. The implantable device of claim 7, wherein the charging component comprises a coil configured to respond to an electric or a magnetic field generated outside the body, wherein the thermal barrier is between the coil and the thermally sensitive portion, wherein the thermal barrier thermally isolates the coil from the thermally sensitive portion so that thermal resistance between the coil and the thermally sensitive portion is above the thermal resistance between the coil and the body.

11. A microstimulator dimensioned to be implanted in a body through a cannula of a surgical tool for performing closed surgical procedures, the microstimulator being configured to deliver electrical pulses to tissue of a body in which the microstimulator is implanted the microstimulator comprising:

a casing;

a charging coil configured to convert an electric field or a magnetic field generated outside the body into potential energy, wherein the conversion is accompanied by a change in temperature the coil disposed on a surface of the casing and having a planar surface that conforms to the surface of the casing;

electrical circuitry contained within the casing to manage delivery of the electrical pulses to the tissue of the body; and a thermal barrier between the charging coil and the electrical circuitry, wherein the thermal barrier thermally isolates the charging coil from the electrical circuitry so that thermal resistance between the charging coil and the electrical circuitry is above the thermal resistance between the charging coil and the body.

12. The microstimulator of claim 11, wherein the thermal conductance between the coil and the body is 1.5 or more times the thermal conductance between the coil and the electrical circuitry.

13. The microstimulator of claim 11, further comprising one or more electrodes for delivering the electrical pulses to the tissue.

* * * * *

UNITED STATES PATENT AND TRADEMARK OFFICE
CERTIFICATE OF CORRECTION

| | | |
|---|---|---|
| PATENT NO. | : 8,165,694 B2 | Page 1 of 1 |
| APPLICATION NO. | : 12/358093 | |
| DATED | : April 24, 2012 | |
| INVENTOR(S) | : Carbunaru et al. | |

It is certified that error appears in the above-identified patent and that said Letters Patent is hereby corrected as shown below:

Title Page;

Paragraph (12) replace Carbanaru et al. with -- Carbunaru et al. --

Paragraph (75) Inventors: replace Rafael Carbanaru, Valley Village, CA (US); Andrew DiGiore, Santa Monica, CA (US); Brett Schleicher, Valencia, CA (US) with -- Rafael Carbunaru, Valley Village, CA (US); Andrew DiGiore, Santa Monica, CA (US); Brett Schleicher, Valencia, CA (US) --

Signed and Sealed this
Nineteenth Day of June, 2012

David J. Kappos
*Director of the United States Patent and Trademark Office*